United States Patent [19]

Homeier et al.

[11] 4,234,455

[45] Nov. 18, 1980

[54] CATALYST PREPARATION

[75] Inventors: Edwin H. Homeier, Maywood; Russell W. Johnson, Villa Park, both of Ill.

[73] Assignee: UOP Inc., Des Plaines, Ill.

[21] Appl. No.: 28,631

[22] Filed: Apr. 9, 1979

[51] Int. Cl.$^3$ .............................................. B01J 31/22
[52] U.S. Cl. .................................... 252/430; 252/428; 252/431 N; 568/451
[58] Field of Search .................... 252/431 N, 428, 430

[56] References Cited

U.S. PATENT DOCUMENTS

| | | | |
|---|---|---|---|
| 2,929,792 | 3/1960 | Arnold et al. | 252/430 |
| 2,976,253 | 3/1961 | Edwards | 252/430 X |
| 3,108,081 | 10/1963 | Gleim et al. | 252/431 N X |
| 3,686,094 | 8/1972 | Laleuf et al. | 252/431 N X |

Primary Examiner—Patrick Garvin
Attorney, Agent, or Firm—James R. Hoatson, Jr.; Raymond H. Nelson; William H. Page, II

[57] ABSTRACT

Highly active catalysts may be prepared by admixing a macrocyclic metal complex with a solid support followed by shaping the resulting admixture and subjecting said admixture to a calcining step at an elevated temperature in the range of from about 400° to about 700° C. in an inert atmosphere. The preparation process is exemplified by the admixture of alumina hydrous oxide with chlororhodium phthalocyaninetetrasulfonate, extruding the catalyst, drying, and thereafter calcining the admixture at a temperature of about 500° C. to provide a catalyst complex.

14 Claims, No Drawings

CATALYST PREPARATION

This invention relates to a process for the preparation of catalytic compositions of matter. More specifically, the invention is concerned with a process for preparing catalytic compositions of matter which possess a high degree of activity and stability.

Many catalytic compositions of matter which are useful in various chemical reactions comprise organometallic complexes which may, if so desired, be composited on a solid support. For example, rhodium or ruthenium containing organometallic complexes are useful as hydroformylation catalysts. The aforesaid organometallic complexes may be impregnated from a solution onto solid supports. However, these catalysts are difficult to prepare inasmuch as the phthalocyanine complexes possess a relatively low solubility in virtually all solvents, and are therefore difficult to use in the steps of impregnating such an organometallic complex on a solid support. Another disadvantage which results in the impregnation type of catalyst preparation is that the impregnated species consist of aggregates of the organometallic complex rather than discrete metal complex species which are supported on the catalyst base. However, it has now been discovered that by utilizing the process or technique of the present invention which is hereinafter described in greater detail, it is possible to limit the degree of aggregation of the metallic species on the catalyst support. The resultant catalyst complex will consist of widely dispersed metal supported on a catalyst base in a discrete form, the process involving the use of various steps which are easily effected and do not require the use of techniques which require large amounts of energy such as that which is required to prepare catalysts, as for example as making metal atom vapors. The catalyst complex which is prepared according to the process of the present invention will possess a high degree of activity and will remain stable over a relatively long period of time thus enabling the catalyst to possess a longer life with the concomitant spending of a lesser amount of money for the entire operation.

It is therefore an object of this invention to provide a process for the preparation of catalyst complexes.

A further object of this invention is to provide a process for preparing catalyst complexes comprising a mixture of a macrocyclic metal complex with a catalyst base.

In one aspect an embodiment of this invention resides in a process for the preparation of a catalyst complex which comprises admixing a macrocyclic metal complex with a solid support material, shaping the resulting admixture, calcining the shaped material, and recovering the resultant catalyst complex.

A specific embodiment of this invention is found in a process for the preparation of a catalyst complex which comprises admixing chlororhodium phthalocyaninetetrasulfonate with hydrated alumina, shaping the resultant mixture, drying the admixture at an elevated temperature, calcining the dried composite at a temperature in the range of from about 400° to about 700° C. in a nitrogen atmosphere, and recovering the resultant catalyst complex.

Other objects and embodiments will be found in the following further detailed description of the present invention.

As hereinbefore set forth the present invention is concerned with a process for preparing a catalyst which possesses a high degree of activity and stability. The process is effected by mixing an appropriate macrocyclic metal complex with an appropriate catalyst base or solid support. Following the admixture of the two components, it is then shaped, dried and subjected to a calcination step at an elevated temperature, preferably in an inert atmosphere. By utilizing the particular steps of the present invention, it is possible to obtain a catalyst complex in which the metallic portion of the catalyst is in a mono-atomic form on the solid support, thus avoiding the disadvantage of having a catalyst in which the organometallic portion of the catalyst complex is in aggregate form on the support.

It is contemplated within the scope of this invention that the macrocyclic organometallic complexes which form one component of the final catalyst composite will include the transition metals of IB and VIII of the Periodic Table. Specific examples of these macrocyclic metallic complexes will include metal phthalocyanines such as cobalt phthalocyanine, cobalt phthalocyaninemonosulfonate, cobalt phthalocyaninedisulfonate, cobalt phthalocyaninetetrasulfonate, rhodium phthalocyanine, rhodium phthalocyaninemonosulfonate, rhodium phthalocyaninedisulfonate, rhodium phthalocyaninetetrasulfonate, ruthenium phthalocyanine, ruthenium phthalocyaninemonosulfonate, ruthenium phthalocyaninedisulfonate, ruthenium phthalocyaninetetrasulfonate, copper phthalocyanine, copper phthalocyaninemonosulfonate, copper phthalocyaninedisulfonate, copper phthalocyaninetetrasulfonate, chlororhodium phthalocyanine, chlororhodium phthalocyaninemonosulfonate, chlororhodium phthalocyaninedisulfonate, chlororhodium phthalocyaninetetrasulfonate, etc., metal prophoryin complexes such as chlororhodium octaethylporphine, chlororhodium mesoporphyrin IX, chlororhodium mesophorphyrin IX, chlororhodium protoporphyrin IX, chlororhodium meso-tetra(4-carboxyphenyl)porphine, chlororhodium tetrasodium-meso(tetrasulfonataphenyl)-porphine, ruthenium uroporphyrin, ruthenium-meso-tetra(4-pyridyl)porphine, chloroiridium-meso-tetraphenylphorphine, iridium-meso-tetra(4-N-methylpyridyl)porphine tetrachloride, cobalt uroporphyrin III octamethylester, cobalt uroporphyrin I octamethylester, etc. It is to be understood that the aforementioned compounds are only representative of the type of transition metal macrocyclic compounds which may be employed as catalysts, and that the present invention is not necessarily limited thereto.

Examples of solid supports which may be used as the catalyst base in preparing the catalyst complex of the present invention will include such compounds as alumina in the form of alpha-alumina, gamma-alumina, eta-alumina, theta-alumina, etc., silica, mixtures of metal oxides such as silica-alumina, silica-magnesia-alumina, silica-magnesia, zirconia, silica-thoria, aluminum-thoria. Other examples of supports which may be used as the catalyst support include each of the preceding materials comixed with a clay. In addition it is also contemplated that zeolites, carbon, diatomaceous earth such as kieselguhr, montmorillonite, etc., or their hydrates may also be used. The solid support may be in any form, powder being the preferred form of the solid support although it is also contemplated that beads, pellets, spheres, etc., may also be used. In contradistinction to prior art methods of preparing catalyst complexes in which a solution of the organometallic component of the catalyst is impregnated on the solid support, the process of the present invention is effected by admixing the solid support with the organometallic component of the complex in either an aqueous or organic solution. Following a thorough admixing of the two components, the resulting admixture, which may be in the form of a paste, is then shaped into the desired form by any means known in the art such as extrusion and dried to remove the solvent. Following the drying step which may be effected at temperatures dependent on the particular solvent employed, and which may range from about 100° to about 200° C., the catalyst composite is then calcined at an elevated temperature which may range from about 400° to about 700° C. for a period of time which may range from about 0.5 up to about 10 hours or more in duration. The calcination of the catalyst complex is preferably effected in an inert atmosphere such as nitrogen, argon, helium, etc. At the end of the calcination period, the catalyst is recovered and utilized for any particular chemical reaction so desired, one particular reaction being hydroformylation of olefinic hydrocarbons in the presence of carbon monoxide and hydrogen. In the preferred embodiment of the invention, the organometallic component of the catalyst complex is present in an amount within the range of from about 5.0 to about 0.05% by weight of the solid support.

The process for effecting the preparation of the catalyst complex of the present invention may be effected in any suitable manner and may comprise either a batch or continuous operation. For example, when a batch type operation is employed, a quantity of the macrocyclic organometallic complex along with the solid support and a predetermined amount of solvent, either aqueous or organic in nature, are placed in an appropriate apparatus and thoroughly admixed. Following the admixture of the two components which may be effected at ambient temperature and atmospheric pressure, the resulting paste is then formed into the desired shape. For example, the paste may be passed through an extruder and thereafter marumerized to form spheres. The shaped particles are then dried at an elevated temperature for example, about 120° C. when water is used as the solvent, for a period of time which may range from about 1 to about 16 hours or more in duration, the amount of time expended being that which is sufficient to remove the aforesaid solvent. Upon completion of the drying step, the shaped particles are then calcined in a calcining operation such as an oven at a temperature in the range of from about 400° to about 700° C. for a period of time which may range from about 0.5 to about 10 hours or more, said calcination being effected under a stream of an inert gas such as nitrogen. Upon completion of the desired calcination step the heating is discontinued and the catalyst is recovered. If so desired, the calcined catalyst complex may be maintained in an inert atmosphere such as that which is supplied by a blanket of nitrogen until the catalyst is ready for use in a predetermined chemical reaction.

It is also contemplated within the scope of this invention that the process for preparing a catalyst complex according to the present invention may be effected in a continuous manner of operation. When such a type of operation is employed, the components of the catalyst complex comprising macrocyclic organometallic complex and a solid support are continuously fed to the mixing zone wherein the components are thoroughly admixed in the presence of a solvent which is present in an amount sufficient to permit the formation of a paste. The thoroughly admixed components in the form of the paste are continuously withdrawn from this mixing zone and passed to a shaping apparatus wherein the paste is formed into the desired shape such as spheres, pellets, etc. The thus formed catalyst complex is then passed to a drying zone wherein the solvent is removed. After passage through the drying zone for a period of time sufficient to effect the removal of the solvent, the dried composite is then continuously passed to a calcination zone wherein the particles are calcined at a temperature within the range hereinbefore set forth under a stream of an inert gas. Following the passage through the calcination zone the calcined particles are then continuously withdrawn and passed to storage prior to use in a predetermined chemical reaction.

The following examples are given for the purposes of illustrating the process of the present invention and the ability of the thus formed catalyst complex to maintain a high activity and relatively long stability. However, it is to be understood that these examples are given merely for purposes of illustration and that the present process is not necessarily limited thereto.

EXAMPLE I

In this example 8 grams of chlororhodium phthalocyaninetetrasulfonate was thoroughly admixed with 666 grams of hydrous alumina and 675 ml of water to produce a paste. Thereafter the paste was extruded and marumerized to form a catalyst complex in the shape of spheres. The resultant blue spheres were dried for a period of 16 hours at a temperature of 120° C. in an air atmosphere. Following this the spheres were then calcined in an oven at a temperature of 500° C. for a period of 1 hour under a stream of nitrogen which was passed over the spheres at a rate of about 1 l/min. During this calcining period a gas which was presumably sulfur trioxide was liberated from the catalyst.

To illustrate the efficiency of the catalyst to maintain a high conversion activity, a 20 cc (11 gram) portion of the catalyst was tested as a hydroformylation catalyst in a standard batch activity test. The hydroformylation reaction was effected in a glass-lined, stainless steel rotating autoclave at a temperature of 80° and an initial operating pressure of 160 atmospheres consisting of equimolar amounts of carbon monoxide and hydrogen. The reaction was effected for a period of 6 hours using 21 grams of decene-5 as the charge stock. At the end of the 6 hour period heating was discontinued, the autoclave was allowed to return to room temperature, and the excess pressure was discharged. After opening the autoclave the resultant tan catalyst and slightly yellow solution were separated by decanting off the bulk of the liquid product. The liquid product was analyzed by means of conventional gas liquid chromatographic technique and disclosed that about 23 wt. % of the decene-5 feed had been converted to undecanal.

The recovered catalyst was washed with acetone to remove residual products and recycled for use in a series of six further standard batch tests. The cumulative results of these six tests are set forth in Table I below.

TABLE I

| Test No. | Cumulative Decene-5 Processed (Grams) | Wt. % Yield of Undecyl Aldehyde | Soluble Rhodium in Mols/l × $10^4$ | Product Mmols Rh |
|---|---|---|---|---|
| 1 | 21 | 23 | 5.0 | 0.015 |
| 2 | 42 | 100 | 7.2 | 0.021 |
| 3 | 64 | 99 | 7.3 | 0.022 |
| 4 | 86 | 99 | 2.1 | 0.0064 |
| 5 | 107 | 99 | — | — |
| 6 | 127 | 99 | 0.87 | 0.0024 |
| 7 | 147 | 92 | — | — |

EXAMPLE II

To illustrate the ability of the catalyst prepared according to the process of the present invention to maintain a high activity as compared with catalysts prepared according to prior art method, a second catalyst complex was prepared in which an aqueous solution of chlororhodium phthalocyaninetetrasulfonate was impregnated onto a gamma-alumina support. The impregnation was effected at a temperature of 25° C. for a period of 2 hours. At the end of this time the impregnated gamma-alumina was calcined under a stream of nitrogen for a period of 1 hour at a temperature in the range of from about 490° to about 500° C. It was noted that the blue catalyst remained this color instead of turning grey as did the catalyst prepared according to the process set forth in Example I above. In addition, it was also noted that the material which was swept from the surface of the catalyst by the nitrogen stream was basic in nature and not acidic.

The catalyst which was prepared according to the above paragraph was used to catalyze a hydroformylation reaction which was effected in a manner similar to that set forth in Example I above, 50 cc of the catalyst complex being used to treat decene-5 at a temperature of 80° C. and an initial operating pressure of 160 atmospheres, said pressure being reached by the use of equimolecular amounts of carbon monoxide and hydrogen. The results of three batch type activity tests are set forth in Table II below.

TABLE II

| Test No. | Cumulative Decene-5 Processed (Grams) | Wt. % Yield of Undecyl Aldehyde | Soluble Rhodium in Mols/l × $10^4$ | Product Mmols Rh |
|---|---|---|---|---|
| 1 | 22 | 25 | 2.2 | 0.0068 |
| 2 | 45 | 73 | 4.1 | 0.013 |
| 3 | 67 | 48 | — | — |

It is therefore readily apparent from a comparison of the above tables that the catalyst prepared according to the method set forth in Example I above maintained an activity at a high level which contrasted to the activity of a catalyst prepared by merely impregnating a solid support with a solution of the organometallic complex, said figures being evident by a comparison of the wt. % yield of undecyl aldehyde which is obtained in the experiments.

We claim as our invention:

1. A catalyst prepared by admixing a metal phthalocyanine with a solid support material, shaping the resulting admixture, calcining the shaped material at a temperature of from about 400° C. to about 700° C., and recovering the resultant catalyst.
2. The catalyst as set forth in claim 1 in which said solid support is an alumina.
3. The catalyst as set forth in claim 2 in which said alumina is gamma-alumina.
4. The catalyst as set forth in claim 2 in which said alumina is alpha-alumina.
5. The catalyst as set forth in claim 1 in which said solid support material is carbon.
6. The catalyst as set forth in claim 1 in which said solid support is a zeolite.
7. The catalyst as set forth in claim 1 in which said solid support is a silica-alumina.
8. The catalyst as set forth in claim 1 in which said metal phthalocyanine is rhodium phthalocyanine.
9. The catalyst as set forth in claim 1 in which said metal phthalocyanine is rhodium phthalocyaninetetrasulfonate.
10. The catalyst as set forth in claim 1 in which said metal phthalocyanine is chlororhodium phthalocyaninetetrasulfonate.
11. The catalyst as set forth in claim 1 in which said metal phthalocyanine is ruthenium phthalocyaninetetrasulfonate.
12. The catalyst as set forth in claim 1 in which said metal phthalocyanine is ruthenium phthalocyanine.
13. The catalyst as set forth in claim 1 in which said calcination is effected in an inert atmosphere.
14. The catalyst as set forth in claim 13 in which said inert atmosphere is nitrogen.

* * * * *